United States Patent
Kimball

(10) Patent No.: US 8,911,773 B2
(45) Date of Patent: *Dec. 16, 2014

(54) PEELABLE POUCH FOR TRANSDERMAL PATCH AND METHOD FOR PACKAGING

(71) Applicant: Watson Laboratories, Inc., Salt Lake City, UT (US)

(72) Inventor: Michael W. Kimball, Salt Lake City, UT (US)

(73) Assignee: Watson Laboratories, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/090,502

(22) Filed: Nov. 26, 2013

(65) Prior Publication Data

US 2014/0076763 A1 Mar. 20, 2014

Related U.S. Application Data

(60) Continuation of application No. 13/036,791, filed on Feb. 28, 2011, now Pat. No. 8,623,404, which is a division of application No. 11/645,115, filed on Dec. 21, 2006, now Pat. No. 7,921,999, which is a continuation-in-part of application No. 10/996,476, filed on Nov. 24, 2004, now abandoned, which is a continuation of application No. 10/321,405, filed on Dec. 16, 2002, now abandoned.

(60) Provisional application No. 60/343,475, filed on Dec. 20, 2001.

(51) Int. Cl.
*A61F 13/00* (2006.01)
*A61K 9/70* (2006.01)

(52) U.S. Cl.
CPC ............ *A61F 13/00063* (2013.01); *A61K 9/703* (2013.01); *Y10S 206/815* (2013.01)
USPC ............ 424/449; 424/443; 424/447; 206/815

(58) Field of Classification Search
CPC .............. A61J 2001/00; A61J 2205/50; A61J 2001/1412; A61J 2001/1431; A61J 2001/1468; A61J 1/10; A61J 1/12; A61J 3/00; A61B 19/02; A61K 9/7023; A61K 9/703; A61K 9/7038; A61K 9/7053; A61M 35/00; A61M 35/003; A61M 35/006
USPC ........................... 424/443–449; 206/815, 826
See application file for complete search history.

(56) References Cited

U.S. PATENT DOCUMENTS

| | | | |
|---|---|---|---|
| 2,954,116 A | 9/1960 | Maso et al. |
| 2,998,880 A | 9/1961 | Ladd |
| 3,057,467 A | 10/1962 | Williams |
| 3,124,825 A | 3/1964 | Iovenko |
| 3,152,515 A | 10/1964 | Land |
| 3,152,694 A | 10/1964 | Nashed et al. |
| 3,186,869 A | 6/1965 | Friedman |
| 3,217,871 A | 11/1965 | Lee |
| 3,403,776 A | 10/1968 | Denny |
| 3,478,868 A | 11/1969 | Nerenberg et al. |
| 3,552,638 A | 1/1971 | Quackenbush |
| 3,563,371 A | 2/1971 | Heinz |
| 3,616,898 A | 11/1971 | Massie |
| 3,708,106 A | 1/1973 | Sargent |
| 3,847,280 A | 11/1974 | Poncy |
| 3,913,789 A | 10/1975 | Miller |
| 3,926,311 A | 12/1975 | Laske |
| 3,937,396 A | 2/1976 | Schneider |
| 3,995,739 A | 12/1976 | Tasch et al. |
| 4,279,344 A | 7/1981 | Holloway, Jr. |
| 4,410,089 A | 10/1983 | Bortolani |
| 4,552,269 A | 11/1985 | Chang |
| 4,656,068 A | 4/1987 | Raines |
| 4,849,224 A | 7/1989 | Chang et al. |
| 4,855,294 A | 8/1989 | Patel et al. |
| 4,964,515 A | 10/1990 | Heyden |
| 4,983,395 A | 1/1991 | Chang et al. |

(Continued)

FOREIGN PATENT DOCUMENTS

| GB | 515876 | 12/1939 |
|---|---|---|
| GB | 1 508 492 | 4/1978 |

(Continued)

OTHER PUBLICATIONS

Photograph of Schwarz Pharma's Neupro (rotigotine) transdermal patch, expiration date of Dec. 2007; Applicant believes this product was offered for sale prior to Dec. 21, 2006.

*Primary Examiner* — Michael G Hartley
*Assistant Examiner* — Micah-Paul Young
(74) *Attorney, Agent, or Firm* — Florek & Endres PLLC

(57) ABSTRACT

A peelable pouch comprises a substantially flat enclosure formed by first and second opposing flexible plies. A seat extends along at least a portion of a perimeter of the opposing plies. A flat, flexible transdermal patch is disposed in the enclosure and includes a bioactive agent dissolved in a layer of adhesive. A release liner is removably attached over the layer of adhesive, with the patch and the release liner together being sufficiently resilient so as to generate a spring force when displaced out of the flat configuration. The first and the second plies each being separable along the seal and displaceable out of the flat configuration. The spring force generated by the patch and the release liner being sufficient to overcome an adhesive force created by the adhesive between the patch and one of the plies.

26 Claims, 8 Drawing Sheets

(56) References Cited

U.S. PATENT DOCUMENTS

| | | |
|---|---|---|
| 5,077,104 A | 12/1991 | Hunt et al. |
| 5,122,383 A | 6/1992 | Heiber et al. |
| 5,131,760 A | 7/1992 | Farmer |
| 5,152,997 A | 10/1992 | Ebert et al. |
| 5,164,190 A | 11/1992 | Patel et al. |
| 5,181,610 A | 1/1993 | Quick et al. |
| 5,227,169 A | 7/1993 | Heiber et al. |
| 5,253,754 A | 10/1993 | Soodak |
| 5,266,371 A | 11/1993 | Sugii et al. |
| 5,341,922 A | 8/1994 | Cerwin et al. |
| 5,366,296 A | 11/1994 | Stenstrom et al. |
| 5,411,740 A | 5/1995 | Lee et al. |
| 5,460,820 A | 10/1995 | Ebert et al. |
| 5,500,222 A | 3/1996 | Lee et al. |
| 5,532,278 A | 7/1996 | Aberg et al. |
| 5,562,642 A | 10/1996 | Smith et al. |
| 5,601,839 A | 2/1997 | Quan et al. |
| 5,613,958 A | 3/1997 | Kochinke et al. |
| 5,633,008 A | 5/1997 | Osborne et al. |
| 5,677,346 A | 10/1997 | Aberg et al. |
| 5,686,097 A | 11/1997 | Taskovich et al. |
| 5,736,577 A | 4/1998 | Aberg et al. |
| 5,747,065 A | 5/1998 | Lee et al. |
| 5,750,137 A | 5/1998 | Taskovich et al. |
| 5,762,953 A | 6/1998 | Venkateshwaran |
| 5,780,050 A | 7/1998 | Jain et al. |
| 5,783,208 A | 7/1998 | Venkateshwaran et al. |
| 5,834,010 A | 11/1998 | Quan et al. |
| 5,846,558 A | 12/1998 | Nielsen et al. |
| 5,900,250 A | 5/1999 | Lee et al. |
| 5,948,433 A | 9/1999 | Burton et al. |
| 5,950,830 A | 9/1999 | Trigger |
| 6,010,715 A | 1/2000 | Wick et al. |
| 6,059,112 A | 5/2000 | Dykstra et al. |
| 6,129,929 A | 10/2000 | Wick |
| 6,159,496 A | 12/2000 | Blanchard et al. |
| 6,159,497 A | 12/2000 | LaPrade et al. |
| 6,231,885 B1 | 5/2001 | Carrara |
| 6,267,983 B1 | 7/2001 | Fujii et al. |
| 6,326,069 B1 * | 12/2001 | Barnett et al. ............. 428/35.7 |
| 6,676,961 B1 | 1/2004 | Lichter |
| 6,905,016 B2 | 6/2005 | Kanios et al. |
| 6,974,588 B1 | 12/2005 | Miranda et al. |
| 7,921,999 B1 * | 4/2011 | Kimball ................. 206/440 |
| 8,151,987 B2 * | 4/2012 | Kimball ................. 206/440 |
| 8,623,404 B2 * | 1/2014 | Kimball ................. 424/449 |
| 2001/0031787 A1 | 10/2001 | Hsu et al. |
| 2001/0051166 A1 | 12/2001 | Luo et al. |

FOREIGN PATENT DOCUMENTS

| | | |
|---|---|---|
| GB | 2 272 877 | 6/1994 |
| JP | 54-115997 | 9/1979 |
| WO | 85/03275 | 8/1985 |
| WO | 90/05683 | 5/1990 |
| WO | 90/11065 | 10/1990 |
| WO | 93/00274 | 1/1993 |

* cited by examiner

PEELABLE POUCH FOR TRANSDERMAL PATCH AND METHOD FOR PACKAGING

This application is a continuation of U.S. patent application Ser. No. 13/036,791, filed Feb. 28, 2011, issued as U.S. Pat. No. 8,623,404; which in turn is a divisional of U.S. patent application Ser. No. 11/645,115, filed Dec. 21, 2006, issued as U.S. Pat. No. 7,921,999; which is a continuation-in-part of U.S. patent application Ser. No. 10/996,476, filed Nov. 24, 2004, abandoned; which is a continuation of U.S. patent application Ser. No. 10/321,405, filed Dec. 16, 2002, abandoned; which claims benefit of U.S. Provisional Patent Application Ser. No. 60/343,475, filed Dec. 20, 2001; all of which are incorporated herein in their entirety.

BACKGROUND OF THE INVENTION

1. Field of the Invention

The present invention relates generally to peelable pouches for storage of transdermal patches, and methods for packaging objects or transdermal patches.

2. Related Art

Transdermal systems often include medicine or another bioactive agent that is absorbed by the user's skin over a period of time. A typical transdermal system can include an adhesive skin patch containing medicine that passes from the patch and through the user's skin. Such patches often are provided in a package formed of a pair of plies of material that are sealed together about their perimeters. A thin space is disposed between the sealed plies in which the transdermal patch is located.

One disadvantage with transdermal systems, or the packaging thereof, is the difficulty in removing the patch from the package for use. Typically, the perimeter of the package is scored or notched near a corner to facilitate breaking or tearing the sealed plies and opening the package. The user can grasp the package adjacent either side of the score or notch, and tear off a portion of the package to reveal the thin space with the transdermal patch therein.

It will be appreciated that such transdermal patches often include an adhesive used to affix the patch to the user's skin. Over time, a minimal amount of such adhesive can seep out about a perimeter of the patch, causing the patch itself to adhere to an inner surface of the package. Thus, as the user tears off a portion of the package to reveal the thin space and patch therein, the patch can be adhered to a surface of the package instead of being freely exposed within the space, resisting convenient removal of the patch. Although the packaging typically includes an inner surface of foil, or other "non-stick" surface such as a polymer coating, to resist adherence of the patch to the packaging, the adhesive often is capable of lightly adhering to such surfaces, or is capable of providing sufficient adherence to thwart or prevent removal of the patch.

It also will be appreciated that such patches, and thus such packages, can be small enough that the thin space therein is small enough to prevent or hinder the user from inserting his or her fingers and grasping the patch. In addition, as stated above, the patch can become adhered to the inner surface the package, thus further preventing or resisting the user's attempt to grasp the patch, even if sufficient space exists to insert fingers.

In addition, the user often must engage in further operations to further open the package and retrieve the patch. For example, after having torn the first portion of the package to obtain access to the space and the patch, the user often must further tear the package in order to increase the opening to the space, or further reveal the patch, in order to increase access to grasp the patch or separate it from the inner surface of the package. Such further manipulation of the packaging increases the risk of molesting or damaging the patch.

Another disadvantage with such transdermal systems, or packaging, is that the tear method of opening the package increases the risk of tearing the package across the transdermal patch itself, thus tearing or molesting the patch.

Another disadvantage with such transdermal systems is that packaging configured for one type of transdermal system may not be sufficient to package another. For example, one package configured to prevent leakage of a first type of medicine may not sufficiently prevent leakage of a second type of medicine because such packaging may not contain the second type of medicine.

SUMMARY OF THE INVENTION

The invention provides a peelable pouch, including a substantially flat enclosure formed by first and second opposing flexible plies. A seal can extend along at least a portion of a perimeter of the opposing plies. A flat, flexible transdermal patch can be disposed in the enclosure, the patch including a bioactive agent dissolved in a layer of adhesive. A release liner can be removably attached over the layer of adhesive. The patch and the release liner can together be sufficiently resilient so as to generate a spring force when displaced out of the flat configuration. The first and the second plies can each be separable along the seal and can be displaceable out of the flat configuration. The spring force generated by the patch and the release liner can be sufficient to overcome an adhesive force created by the adhesive between the patch and one of the plies.

In accordance with another aspect of the invention, a peelable pouch is provided, including a substantially flat enclosure formed by first and second opposing flexible plies. A seal can extend along at least a portion of a perimeter of the opposing plies and can couple the plies to one another. A flexible transdermal patch can be disposed in the enclosure, the patch including a bioactive agent dissolved in a layer of adhesive. A release liner can be removably attached over the layer of adhesive. The patch and the release liner can together be sufficiently rigid so as to at least partially resist bending, and can be sufficiently resilient so as to return to a substantially flat orientation after being bent out of the flat configuration. The first and the second plies can each be separable along the seal and displaceable out of the flat configuration.

In accordance with another aspect of the invention, an oxybutynin medicine system is provided, including first and second opposing flexible plies forming an enclosure. A seal can extend along at least a portion of a perimeter of the opposing plies with an enclosed cavity between the plies. First and second opposing tabs, formed by a portion of the respective first and second opposing plies, can extend beyond the seal. An oxybutynin transdermal patch can be disposed in the enclosed cavity between the first and second opposing plies. The transdermal patch can include i) a substrate; ii) an adhesive layer disposed on the substrate and configured to adhere the substrate to a users skin; iii) oxybutynin dissolved in the adhesive layer; and iv) a release liner, removably disposed over the adhesive layer and the oxybutynin dissolved therein. The oxybutynin, and/or a permeation enhancer, can interact with the adhesive layer and can cause the adhesive therein to i) lose cohesion, ii) seep beyond a perimeter of the patch, and iii) adhere to at least one of the two plies of the pouch. The seal can include a polyacrylonitrile copolymer resin. The first and second opposing flexible plies can have: i)

a closed configuration in which a majority of the two plies are disposed in a planar layer; and ii) an open configuration in which at least a portion of the two plies are separated along the seal and pulled out of the planar layer and back across the planar layer to present the oxybutynin transdermal patch between the two plies.

There has thus been outlined, rather broadly, relatively important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Figure 1:
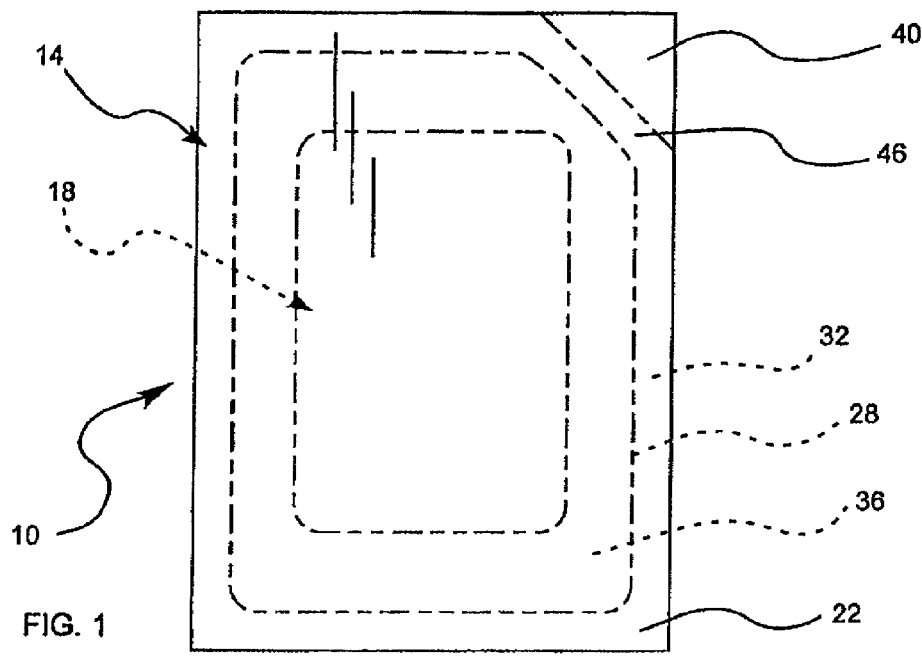
FIG. 1 is a front view of a preferred embodiment of a peelable pouch in accordance with the present invention.
Figure 2:
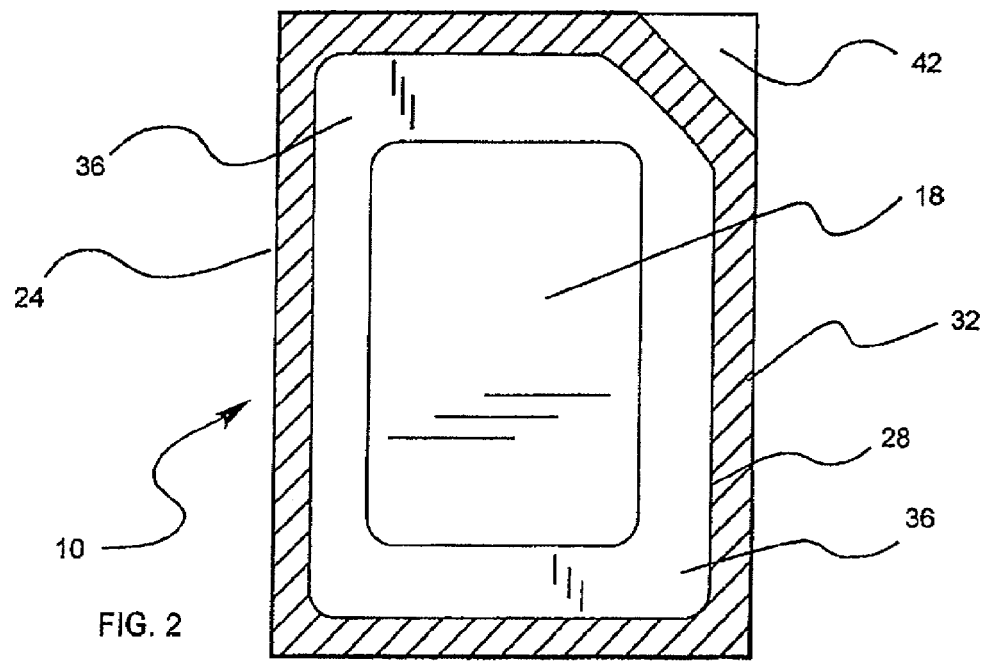
FIG. 2 is a front view of the peelable pouch of FIG. 1 with one ply of the pouch removed to reveal a transdermal patch therein.

Before the present invention is disclosed and described, it should be understood that this invention is not limited to the particular structures, process steps, or materials disclosed herein, but is extended to equivalents thereof as would be recognized by those of ordinarily skilled in the relevant arts. It should also be understood that terminology employed herein is used for the purpose of describing particular embodiments only and is not intended to be limiting in any way.

It must be noted that, as used in this specification and the appended claims, the singular forms "a" and "the" include plural referents, unless the context clearly dictates otherwise. Thus, for example, reference to a "medicament" includes one or more of such medicaments.

DEFINITIONS

In describing and claiming the present invention, the following terminology will be used in accordance with the definitions set forth below.

"Topical formulation" means a composition in which the drug may be placed for direct application to a skin surface and from which an effective amount of drug is released. Examples of topical formulations include but are not limited to ointments, creams, gels, transdermal patches, sprays, vaginal rings, and pastes.

"Transdermal" refers to the route of administration that facilitates transfer of a drug through a skin surface wherein a transdermal composition is administered to the skin surface. Transdermal administration can be accomplished by applying, pasting, rolling, attaching, pouring, pressing, rubbing, etc., of a transdermal preparation onto a skin surface. These and additional methods of administration are well-known in the art.

"Transdermal delivery system," "transdermal patches" or simply "patches" refer to a matrix or liquid reservoir type of delivery device which is used to transdermally deliver defined doses of a substance, over a specific application period.

One example of a transdermal patch for administering oxybutynin in accordance with this invention is a matrix-type patch which comprises an occlusive backing that is impermeable to the oxybutynin and defines the face or top surface of the patch and a solid or semisolid matrix layer comprised of a homogeneous blend of the oxybutynin, a polymeric pressure sensitive adhesive carrier, and optionally one or more skin permeation enhancers. Matrix patches are known in the art of transdermal drug delivery. Examples without limitation, of adhesive matrix transdermal patches are those described or referred to in U.S. Pat. Nos. 5,122,383 and 5,460,820, which are incorporated by reference in their entirety.

A transdermal patch for administering male testosterone such as Androderm™, in accordance with this invention, is a liquid reservoir system (LRS) type patch which comprises male testosterone, and other optional ingredients such as a permeation enhancer, in a carrier vehicle. The carrier vehicle comprises a fluid of desired viscosity, such as a gel or ointment, which is formulated for confinement in a reservoir having an impermeable backing and a skin contacting permeable membrane, or membrane adhesive laminate providing diffusional contact between the reservoir contents and the skin. For application, a peelable release liner is removed and the patch is attached to the skin surface. LRS patches are known in the art of transdermal drug delivery. Examples without limitation, of LRS transdermal patches are those described or referred to in U.S. Pat. Nos. 4,849,224 and 4,983,395, which are incorporated by reference in their entirety.

"Skin," "skin surface," "derma," "epidermis," and similar terms are used interchangeably herein, and refer to not only the outer skin of a subject comprising the epidermis, but also to mucosal surfaces to which a drug composition may be administered. Examples of mucosal surfaces include the mucosal of the respiratory (including nasal and pulmonary), oral (mouth and buccal), vaginal, introital, labial, and rectal surfaces. Hence the terms "transdermal" encompasses "transmucosal" as well.

The terms "formulation" and "composition" are used interchangeably herein. The terms "pharmaceutical" and "drug" are also used interchangeably to refer to a pharmacologically active substance or composition. "Bioactive agent", "medicine", "medication", "drug", "prescription" and similar terms are used interchangeably herein. These terms of art are well-known in the pharmaceutical and medicinal arts.

"Permeation enhancer" refers to anything used to assist the transdermal formulation to penetrate the skin. A wide variety of skin penetration enhancers are suitable with a transdermal device being used in the pouch of the present invention. The specific enhancer used may depend largely on the particular transdermal formulation to be employed and may be determined by one of ordinary skill in the art without undue experimentation by considering various factors such as the bioactive agent or drug to be delivered, the specific pharmaceutically acceptable carrier to be used, etc. An index of permeation enhancers is disclosed by David W. Osborne and Jill J. Henke, in their publication entitled "Skin Penetration Enhancers Cited in the Technical Literature," published in *Pharmaceutical Technology* (June 1998), and is incorporated herein by reference.

Examples of suitable penetration enhancers of the present invention include, without limitation: fatty acids, fatty acid esters, fatty alcohols, fatty acid esters of lactic acid or glycolic acid and their salts, amides, amines, pyrrolidones, glycerol triesters, terpenes, classical surfactants, azocyclic compounds, organic acids, complexing agents, biologics and mixtures thereof.

The term "ply" or "plies" refers to one or more layers or sheets of material.

The term "seal" refers to a closure to block access and that must be broken to gain access. Such a seal can be formed chemically, mechanically, or both chemically and mechanically. An example of a seal includes adhering portions or plies of the pouch together by an adhesive or other means. The seal can include resins or resin compositions, such as vinyl resins, polyethylene resin, hydroxyl modified, vinyl chloride-acetate, thermoplastic copolymer resin; thermoplastic materials such as polyethylene, polyvinyl chloride; a polyvinyl acetal such as polyvinyl butyral, polyvinyl acetal, polyvinyl formal; a polyester such as polyalkylene terephthalate (such as Mylar™); polyvinyl alcohol, methyl cellulose, sodium carboxymethylhydroxyethyl cellulose, polyethylene glycol, polyvinyl acetate-chloride copolymer, polyvinylidene chloride, polypropylene, polyimide, or fluorinated ethylene-propylene copolymer.

The seal can be formed by applying heat and/or pressure to the pouch or plies, causing the adhesive or other material to adhere the plies together, and seal the pouch. In addition, the seal can be formed by ultra-sonic welding. In addition, the seal can be corrugated or embossed.

The term "tab" or "tabs" refers to a flap or appendage for grasping and pulling. For example, a portion of the ply or pouch can form a tab.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

Distances, angles, forces, weights, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 inch to about 5 inches" should be interpreted to include not only the explicitly recited values of about 1 inch to about 5 inches, but also include individual values and sub-ranges within the indicated range. This same principle applies to ranges reciting only one numerical value and should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

THE INVENTION

As illustrated in FIGS. 1-5, a peelable pouch 14 in accordance with the present invention is shown for packaging objects. Transdermal patches are one example of a field that may benefit from use of such a peelable pouch 14. Other fields that may benefit from the use of such a peelable pouch 14 include surgical and medical implements, adhesive bandages, syringes, etc. The peelable pouch 14 may form part of a transdermal medicine system 10 with a transdermal patch 18 disposed within the peelable pouch 14.

Bioactive agents or medicines are commonly administered with transdermal patches. In one aspect, the contents of the pouch of the present invention may be a transdermal patch. A variety of transdermal patches are known to those of ordinary skill in the art. For example, U.S. Pat. Nos. 5,122,383 and 5,460,820, which are incorporated by reference in their entirety, disclose various adhesive matrix patches. Further, U.S. Pat. Nos. 4,849,224 and 4,983,395, which are incorporated by reference in their entirety, disclose various Liquid Reservoir System (LRS) type patches. Each of these general types of patches, as well as others, utilizes various structural components, which are known to those skilled in the art.

Figure 6:
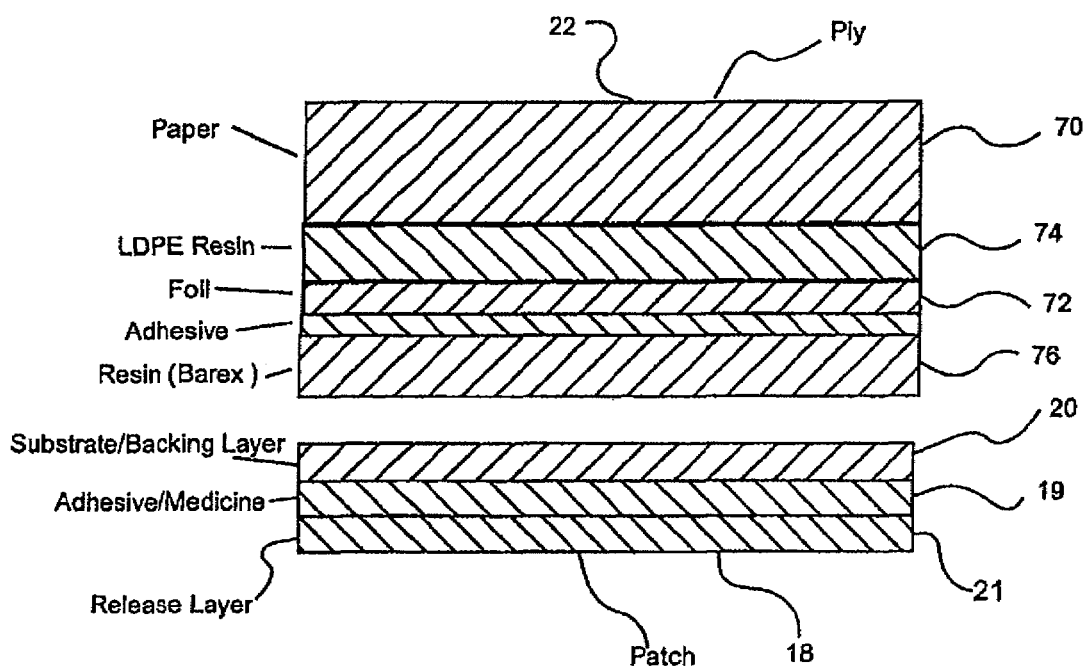
FIG. 6 is a schematic cross sectional view of a ply and a transdermal patch.

As illustrated in FIG. 6, by way of example without limitation, in the case of an adhesive matrix patch 18, an adhesive layer 19 is disposed on a substrate or distal backing 20. The distal backing can be laminated to a polymer layer (not shown). Such a distal backing defines the side of the matrix patch that faces the environment, i.e., distal to the skin or mucosa. The backing layer functions to protect the matrix polymer layer and drug/enhancer composition and to provide an impenetrable layer that prevents loss of drug to the environment. Thus, the material chosen for the backing should be compatible with the polymer layer, drug, and enhancer if any, and should be minimally permeable to any components of the matrix patch. Advantageously, the backing can be opaque to protect components of the matrix patch from degradation from exposure to ultraviolet light. Furthermore, the backing should be capable of binding to and supporting the polymer layer, yet should be pliable enough to accommodate the movements of a person using the matrix patch.

Suitable materials for the backing include, but are not limited to: metal foils, metalized polyfoils, composite foils or films containing polyester such as polyester terephthalate, polyester or aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene and styrene-isoprene copolymers, polyethylene, and polypropylene. In one aspect of the invention, the backing layer may have a thickness of about 0.0005 to 0.01 inch.

Further, a release layer or release liner 21 may be temporarily provided upon the proximal side (side to adhere to the skin) of the adhesive layer. Such a liner provides many of the same functions as the backing layer (20) prior to adhesion of the patch to the skin (the release layer is removed prior to attaching the patch to the skin). In use, the release liner is peeled from the adhesive layer just prior to application, and then is discarded. The release liner can be made of the same materials as the backing layer, or other suitable films coated with an appropriate release surface. Thus, while the backing layer/substrate remains as an integral part of the patch (whether or not the patch is attached to the skin), the release layer must be removed prior to attaching the patch to the skin.

A wide variety of materials known to those skilled in the art of transdermal drug delivery may be used as pharmaceutically acceptable carriers for a transdermal patch. In one aspect the carrier may be a biocompatible polymer. In another aspect, the carrier may be an adhesive. In the case of an adhesive matrix patch, the carrier may be a biocompatible adhesive polymer. The carrier, in some aspects, may contain the drug to be transdermally delivered and a penetration enhancer and other ingredients, such as emollients, etc. In the case of a Liquid Reservoir System (LRS) patch, the carrier forms a gel, or other viscous form suitable for use in an LRS patch, as is known in the art. Such a viscous carrier may contain both the drug to be transdermally delivered as well as a penetration enhancer and other ingredients.

In one aspect, the pressure-sensitive adhesive of the pharmaceutically acceptable carrier is suitable for long-term (e.g., greater than 1 day, about 3-4 days, or for longer periods such as 1-4 weeks) contact with the skin. In another aspect, the pressure-sensitive adhesive of the carrier is suitable for a short-term administration (e.g., for a few minutes to a few hours, less than or equal to 1 day). Such adhesives must be physically and chemically compatible with the particular drug and enhancer, and with any carriers and/or vehicles or other additives incorporated into the drug/enhancer composition. In one aspect of the invention, the adhesives of the pharmaceutically acceptable carrier include, without limitation, acrylic adhesives including cross-linked and uncross-linked acrylic copolymers; vinyl acetate adhesives; natural and synthetic rubbers including polyisobutylenes, neoprenes, polybutadienes, and polyisoprenes; ethylenevinylacetate copolymers; polysiloxanes; polyacrylates; polyurethanes; plasticized weight polyether block amide copolymers, and plasticized styrene-rubber block copolymers or mixtures thereof. In yet another aspect of the invention, contact adhesives for use in the pharmaceutically acceptable carrier layer are acrylic adhesives, such as DuroTak 87-2888 adhesive (National Starch & Chemical Co., Bridgewater, N.J.); and polyisobutylene adhesives such as ARcareJ MA-24 (Adhesives Research, Glen Rock, Pa.) and ethylene vinyl acetate copolymer adhesives.

While the pharmaceutically acceptable carrier of an LRS patch may be of any suitable viscous material known to those skilled in the art of transdermal drug delivery, in one aspect of the present invention, the pharmaceutically acceptable carrier of the liquid reservoir forms a gel.

In addition to containing the drug and penetration enhancer, the pharmaceutically acceptable carrier may comprise a number of other additives, such as diluents, excipients, emollients, plasticizers, skin irritation reducing agents, or a mixture thereof. These types of components, as well as others not specifically recited, are well known in the art for inclusion in various transdermal formulations, and may be added as desired to the transdermal drug delivery system of the present invention in specific types and amounts in order to achieve a desired result.

For example, suitable diluents can include mineral oil, low molecular weight polymers, plasticizers, and the like. Many transdermal drug delivery formulations have a tendency to cause skin irritation after prolonged exposure to the skin, thus addition of a skin irritation reducing agent aids in achieving a composition that is better tolerated by the skin. In one aspect, the skin irritation reducing agent may be glycerin, as disclosed in U.S. Pat. No. 4,855,294, which is incorporated by reference in its entirety.

As described above, such patches are commonly provided in tear packages that are ripped or torn open to obtain access to the patch.

It will be appreciated that while the release layer covers most of the surface of the adhesive layer, the patch or adhesive layer can have a perimeter that is exposed to the surrounding environment. The exposed perimeter sometimes allows a minimal amount of the adhesive to escape from the patch beyond the release liner. The escaped adhesive can cause the patch to adhere to the interior of the packaging, thus thwarting or hindering efforts to remove the patch from the packaging for use.

In addition, it has been discovered that certain bioactive agents or medicines, or other ingredients thereof, can cause the adhesive in which it is dissolved to lose cohesion, and seep out of the perimeter of the patch (between the patch and the substrate/backing layer), to a greater extent, thus further aggravating or exasperating the problem of seepage of adhesive. For example, it has been discovered that oxybutynin, and/or a permeation enhancer, causes certain adhesives to lose cohesion and seep or flow more so than other bioactive agents or medicines. Thus, it has been observed that oxybutynin transdermal patches have more frequent occurrences of seepage, and thus adherence to packaging, and/or greater adhesion to the packaging. As discussed above, such adhesion hinders removal of the patch from the packaging, and can result in molestation of the patch as the user rips, tears, or otherwise mutilates the packaging to remove the patch.

In one aspect, the peelable pouch 14 of the present invention advantageously is configured to facilitate opening and removal of a transdermal patch contained therein, and to accommodate the tendency of transdermal patches, such as those with oxybutynin, to adhere to the packaging. Referring again to FIGS. 1 & 2, the peelable pouch 14 includes first and second opposing plies 22 and 24 forming an enclosure 28. The first and second plies 22 and 24 can be separate plies, or separate sheets of material. Alternatively, the plies 22 and 24 may be part of a single sheet of material, folded to have the opposing plies.

Figure 3:
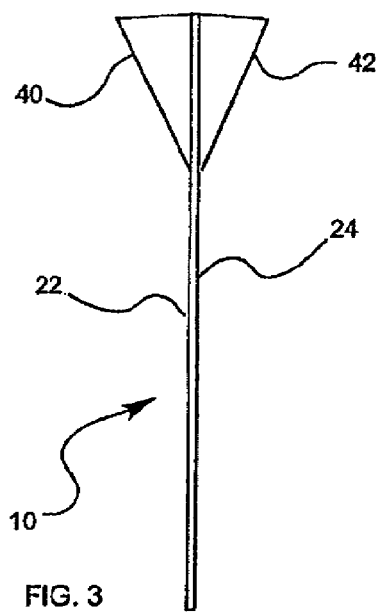
FIG. 3 is a side view of the peelable pouch of FIG. 1 shown in a first closed configuration.

A seal 32 is formed along at least a portion of a perimeter of the plies 22 and 24 sealing at feast a portion of the plies together. In one aspect, the seal 32 extends along nearly the entire perimeter of the plies. An enclosed cavity 36 is formed between the opposing plies 22 and 24, and the seal 32. The transdermal patch 18 is received within the enclosure 28 or cavity 36. The peelable pouch 14, enclosure 28, and/or plies 22 and 24 have a closed configuration, as shown in FIGS. 1 and 3, in which the pouch 14 is sealed and the patch 18 is contained within the enclosure 28.

The transdermal patch 18 preferably is flexible to conform to the contours of the user's body or skin, but initially is flat to reduce space for packaging and shipping. In addition, the plies 22 and 24 and the enclosure 28 may define a substantially or mostly flat, planar layer containing the patch 18, and the plies 22 and 24. In one aspect, the patch 18 and the plies 22 and 24 have a rectangular or square shape to facilitate manufacturing and packaging, but it is contemplated that the patch and plies can have any desired shape.

In one aspect of the invention, portions of the plies 22 and 24 can extend beyond the perimeter or the seal 32 to form first and second opposing tabs 40 and 42. The tabs 40 and 42 are sized large enough to facilitate being grasped by the user. Thus, the tabs 40 and 42 can have a size approximately equal to the tips of a user's fingers. As stated above, the seal 32 can extend around a majority of the perimeter of the plies 22 and 24 or the enclosure 28. A portion 46 of the seal 32, however, can be indented from, or formed away from, a portion of the perimeter of the plies 22 and 24 to form the tabs 40 and 42. In one aspect, the portion 46 of the seal 32 transverses a corner of the plies 22 and 24, leaving the corners of the plies unsealed, to form the tabs 40 and 42.

As stated above, typical packaging can make removing the patch difficult and increases the risk of molesting the patch. In addition, patches often have a tendency to adhere to one side of the packaging, frustrating removal of the patch. The peelable pouch 14, enclosure 28, and/or plies 22 and 24 of the present invention advantageously have an open configuration, as shown in FIGS. 4 and 5, in which portions 50 and 52 of the plies 22 and 24 are separated along the seal 32 in opposite directions, and the transdermal patch 18 is presented extending from the pouch 14 or enclosure 28, between the plies 22 and 24.

Figure 4A:
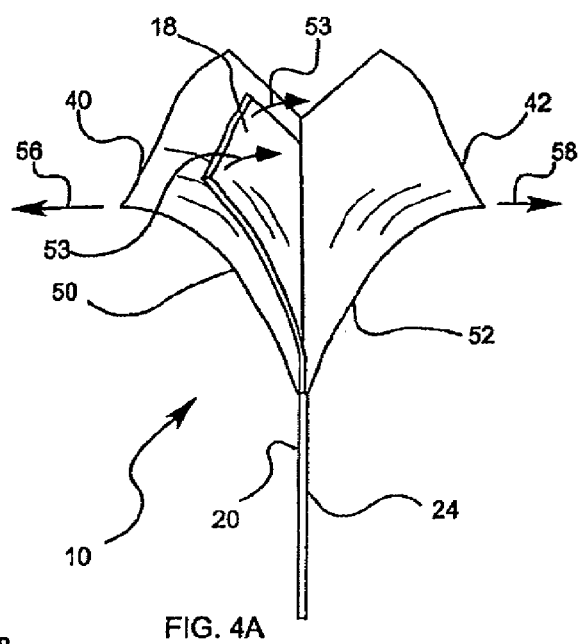
FIG. 4A is a side view of the peelable pouch of FIG. 1, shown in an intermediate configuration as the plies are separated from one another.
Figure 4B:
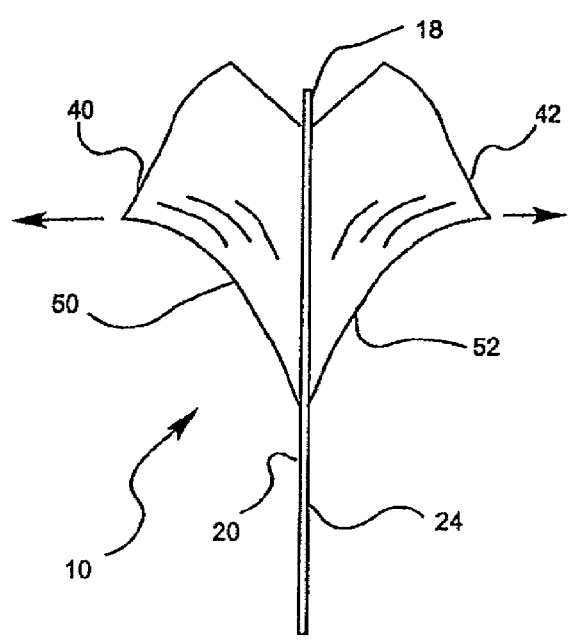
FIG. 4B is a side view of the peelable pouch of FIG. 4A, shown in a second, open configuration presenting the transdermal patch.
Figure 5:
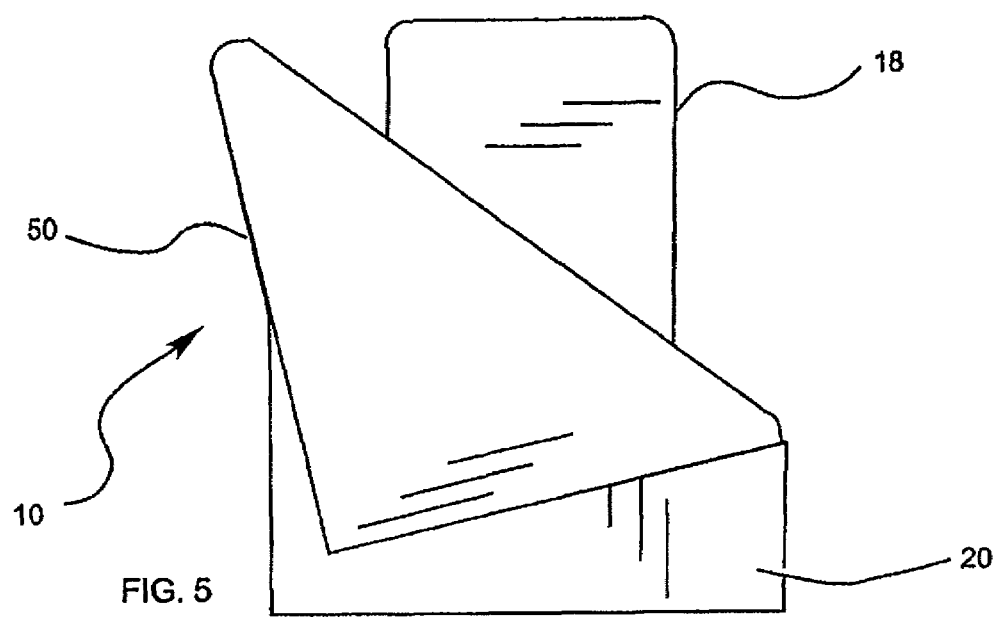
FIG. 5 is a front view of the peelable pouch of FIG. 1 shown in the second open configuration presenting the transdermal patch.

To open the pouch 14, the user grasps the opposing tabs 40 and 42 with fingers of opposite hands, and pulls the tabs 40 and 42, and thus the plies 22 and 24, in a natural direction, which is outwardly approximately perpendicularly or orthogonally to the planar layer of the plies 22 and 24, indicated by arrows 56 and 58 in FIG. 4A. As the user pulls on the tabs 40 and 42, the plies 22 and 24 separate from one another along the seal 32, and the opened portions 50 and 52 are formed.

As the user continues to pull, the tabs 40 and 42, and the open portions 50 and 62, extend back across the pouch 14 or plies 22 and 24. The inventor has found that the outward and backward movement of the open portions 50 and 52 of the plies 22 and 24 tends to cause the open portions 50 and 52 to pull away from any portions of the patch 18 that may be adhered to one or both of the plies.

Although the patch 18 can be flexible, it also is resilient enough to develop a spring force if it is bent backwardly along with one of the plies, such that the developed spring force overcomes any adherence to the ply, and causes the patch 18 itself to pull away from the plies, as shown in FIG. 4A. In this aspect of the invention, the plies 22, 24 can be more flexible (or more easily bent) than the patch by itself. In this manner, an operator can peel the ply away from the patch, without having to touch the patch, by pulling one or both of the plies at a sharp angle relative to the patch and separating the patch from the plies.

In addition, it is believed that the backward movement of the open portion 50 and 52 of the plies 22 and 24 is in a direction along the plane of the patch 18 where the patch is most rigid, causing the plies to separate from the patch, rather than tending to bend the patch. Therefore, when the plies 22 and 24 are separated, a portion of the patch 18 extends outwardly from the pouch 14, enclosure 28, and/or plies 22 and 24, substantially in the planar layer, and presented between the plies 22 and 24 such that it can be easily grasped by the user.

This concept is illustrated schematically in the progression shown from FIG. 3 to FIG. 4A to FIG. 4B. As shown in FIG. 3, initially the tabs 40, 42 can be grasped by the user so that the user can separate the tabs, and thus the plies, along the seal. As shown in FIG. 4A, the initial separation of the plies may result in the patch remaining adhered to one of the plies and bending along with the ply. However, due to the difference in rigidity between the patch and the ply, a restoring spring force (illustrated schematically by directional indicators 53) is created in the patch as it is bent with the ply. The spring force is sufficient to cause the patch (together with the liner) to peel away from the ply (that is being held by fingers of the user), resulting in the patch being presented, in a "free" state, for removal by the user from between the plies.

The spring force created in the patch 18 can be induced in a number of manners. In one aspect of the invention, the material of the patch and/or the liner is selected to provide sufficient rigidity to overcome any adhesion caused by adhesive leeching from the patch. In another aspect, a geometric configuration, including a width, of the patch can be selected to provide the proper spring force for the adhesive being used. The adhesive used can also be varied to ensure that the proper restoring spring force is provided.

In one embodiment of the invention, the patch is formed of an adhesive containing oxybutynin and a permeation enhancer, and a polyester-ethylene vinyl acetate backing layer with an overall thickness on the order of 4 mils, and the liner is formed of a polyester material with a thickness on the order of 3 mils. The plies can be formed of paper, low-density polyethylene, foil, adhesive, and/or Barex with a thickness on the order of 4 mils. In this embodiment, it has been found that spring force generated by deflecting or bending the patch is sufficient to overcome any adhesive force applied when utilizing an adhesive material comprising hexamethyleneglycol dimethacrylate, 2-ethyl hexylacrylate and N-vinyl pyrrolidone.

Generally, however, the patch will be presented between the plies that have each been displaced outwardly from the patch, so that the patch is not "stuck" to any one ply and need not be peeled by hand from the particular ply. Attempting to peel the patch by hand from a ply to which it is adhered is a procedure that can result in contamination of the user's fingers, and can risk damaging the patch in the event the patch is relatively securely attached to the particular ply.

In accordance with one aspect of the present invention, the transdermal system can be an oxybutynin medicine system, and the transdermal patch can be an oxybutynin transdermal patch. Oxybutynin can be used to treat urinary incontinence, or overactive bladder. The oxybutynin is dissolved in the adhesive layer of the patch. As stated above, it has been found that oxybutynin, and/or the associated permeation enhancer or other ingredients, can cause the adhesive to lose cohesion, seep beyond a perimeter of the patch, and adhere to the plies of the pouch (but still satisfy its specifications with respect to the FDA). Thus, the configuration of the pouch 14 of the present invention is well suited to facilitate opening.

Referring to FIG. 1, the seal 32 between the plies 22 and 24 of the pouch 14 for an oxybutynin patch can include a polyacrylontrile copolymer resin, such as Barex® made by British Petroleum, because it has been found to contain the oxybutynin in a satisfactory manner. In addition, referring to FIG. 6, the plies can be formed of a three-ply laminate including an outer layer 70 of coated paper, a core layer 72 of foil, and a laminate 74 of low density polyethylene (LDPE). The outer layer of coated paper provides structural stiffness and a printable surface. In one aspect, the outer layer is 26 lb. C1S paper. The core layer of foil provides a barrier to moisture, gas, and light. The polyethylene layer provides adhesion between the paper and foil, and support for the foil. A layer 76 of the polyacrylontrile copolymer resin, such as Barex®, is disposed over the foil, attached with an adhesive layer, and provides chemical inertness as well as a sealing medium.

In accordance with another aspect of the present invention, the transdermal system can be an estradiol medicine system, and the transdermal patch can be an estradiol transdermal patch. Estradiol, such as Alora®, can be used in female hormone replacement therapy, and to treat osteoporosis. The plies can be formed of an outer layer of coated paper, a core layer of foil, and a laminate of polyethylene (PE). In one aspect, the seal includes a layer of Surlyn® because it has been found to adequately contain estradiol.

In accordance with another aspect of the present invention, the transdermal system can be a liquid reservoir system (LRS), as opposed to a matrix patch, and can include male testosterone, such as Androderm™. Male testosterone can be used to treat male hypogonadism or testosterone deficiency. Again, the plies can include an outer layer of coated paper, a core of foil, and a laminate of polyethylene (PE). The seal can include a low density polyethylene (LDPE) because it has been found to adequately contain Androderm™.

It is of course understood that other bioactive agents can be accommodated. For example, the transdermal patch can include a female testosterone patch for treating women with a hormone replacement therapy regiment. As another example, the transdermal patch can include an anti-fungal agent for toenails or fingernails, such as fluconazole. As another example, the transdermal patch can be used in pain relief, and can include medicines such as fentanyl, morphine, and others. In one aspect of the invention, the bioactive agent can include pramipexole, a dopamine agonist indicated for the treatment of the signs and symptoms of idiopathic Parkinson's disease.

In general, drugs for use in the present composition include therapeutic agents in all of the therapeutic areas including, but not limited to: antibiotics (including antimicrobials, antibacterials, antimycobacterials, antimalerials, antiamebics, anthelminics, antifungals, and antivirals), neoplastic agents, agents affecting the immune response (including steroidal and non-steroidal anti-inflammatory agents), blood calcium regulators, peptide and protein hormones, agents useful in glucose regulation, antithrombotics and hemostatics, antihyperlipidemic agents, thyromimetic and antithyroid drugs, antiulcer agents, histamine receptor agonists and antagonists, inhibitors of allergic response, local anesthetics, analgesics and analgesic combinations, antipsychotics, anti-anxiety agents, antidepressants agents, anorexigenics, bone-active agents, diagnostic agents, and a mixture thereof. Additional examples include: antidiarrheals, antimigraine preparations, antimotion sickness agents, antinauseants, antiparkinsonism drugs, antipruritics, antipyretics, antispasmodics (including gastrointestinal, urinary, skeletal, and smooth-muscle), anti-cholinergics, sympathomimetics, xanthine derivatives, cardiovascular preparations (including calcium channel blockers, beta-blockers, antiarrythmics, antihypertensives, diuretics, vasodilators including general coronary, peripheral and cerebral), central nervous system stimulants including cough and cold preparations, decongestants, diagnostics, hormones, immunosuppressives, parasympatholytics, parasympathomimetics, sedatives, tranquilizers and mixtures thereof.

Examples of specific drugs include without limitation: antibiotics: amoxicillin, cloxacillin sodium, penicillin G potassium; antimicrobials: benzalkonium chloride, chlorohexidine, gluconate hexachlorophene; antibacterials: sulfabenzamide, sulfadiazine, sulfasalazine; antimycobacterials: chlofazimine, ethambutol, isoniazid; antimalerials: chloroquine hydrochloride, quinine sulfate, pyrimethamine; antiamebics: arsthinol, bialamicol, carbarsone; anthelminics: ivermectin, bithionol, piperazine; antifungals: clotrimazole, griseofulvin, miconazole; antivirals: acyclovir, foscarnet sodium, ribavirin; neoplastic agents: adriamycine, cyclophosphamide, methotrexate; immune response steroidal anti-inflammatory agents: hydrocortisone, dioxyanthranol, betamethasone; non-steroidal anti-inflammatory agents (NSAIDs): choline salicylate, diflunisal, ibuprofen, acetaminophen; blood calcium regulators: parathyroid hormone, calcifediol, calcitonin; peptide and protein hormones: insulin, glucagon, vasopressin; glucose regulators: tolazamide, tolbutamide, chlorpropamide; antithrombotics: aspirin, sulfinpyrazone, dipyridamole; hemostatics: thrombin, microfibrillar collagen, absorbable gelatin powder; antihyperlipidemic agents: pravastatin sodium, simvastatin, clinofibrate; thyromimetic and antithyroid drugs: methimazole, propylthiouracil, potassium iodide; antiulcer agents: metoclopramide, histidine hydrochloride, famotidine; histamine receptor agonists and antagonists: astemizole, clemastine fumarate, cyclizine; allergic response inhibitors: astemizole, clemastine fumarate, diphenhydramine hydrochloride; local anesthetics: chloroprocaine hydrochloride, lidocaine hydrochloride, lidocaine base, procaine hydrochloride; analgesics and analgesic combinations: acetaminophen, aspirin, ibuprofen; antipsychotics: acetophenazine maleate, chlorprothixene, droperidol; anti-anxiety agents: diphenhydramine, phenobarbital, chlordiazepoxide; anti-depressants: amitriptyline hydrochloride, amoxapine, fluoxetine hydrochloride; anorexigenics: amphetamine, methamphetamine, chlorphentermine; bone-active agents: parathyroid hormone, calcitonin; diagnostic agents: benzylpenicloyl polylysine, iocetamic acid, aminohippurate sodium; antidiarrheals: diphenoxylate hydrochloride, loperamide hydrochloride, fennel oil; antimigraine preparations: dihydroergotamine mesylate, ergotamine tartrate, methysergide maleate, sumatriptin succinate; antimotion sickness agents: buclizine hydrochloride, diphenidol, meclizine hydrochloride; antinauseants: benzquinamide hydrochloride, dronabinol, dimenhydrinate; antiparkinsonism drugs: amantadine hydrochloride, pramipexole, ropinirole, rotigotine benztropine mesylate, biperiden hydrochloride; antipruritics: camphor, menthol, pramoxine; antipyretics: acetaminophen, aspirin, ibuprofen; antispasmodics (including gastrointestinal, urinary, skeletal and smooth-muscle): flavoxate, flavoxate hydrochloride, ethaverine hydrochloride, oxybutynin chloride, dicyclomine; anti-cholinergics: propantheline, oxybutynin, oxybutynin hydrochloride, adiphenine hydrochloride, aminopentamide, atropine; sympathomimetics: dopamine hydrochloride, epinephrine, ephedrine sulfate; xanthine derivatives: caffeine, theophylline, aminophylline; calcium channel blockers: amlodipine, felodipine, isradipine, diltiazem, nifedipine; beta blockers: propanolol, pindolol, labetalol, betaxolol; anti-arrythmics: procainamide, prajmaline, disopyramide; antihypertensives: clonidine hydrochloride, clonidine base, guanabenz acetate, methyldopa; diuretics: ammonium chloride, mannitol, urea, hydrochlorothiazide, bumetanide; vasodilators: (general) diazoxide, minoxidil, pinacidil; (Coronary) amotriphene, bendazol, benfurodil hemisuccinate; (Peripheral) bamethan, bencyclane, betahistine; (Cerebral) bencyclane, cinnarizine, citicoline; central nervous system (CNS) stimulants cough and cold preparations: dextromethorphan hydrobromide; decongestants: pseudoephedrine hydrochloride, diphenhydramine hydrochloride; chlorpheniramine maleate; hormones: estradiol, norelgestromin, corticosteroids, hydrocortisone; testosterone, progesterone; immunosuppressives: cyclosporin, mizoribine, brequinar sodium; parasympatholytics: atropine sulfate, belladonna, cyclopentolate hydrochloride; parasympathomimetics: pyridostigmine, physostigmine, scopolamine; sedatives: buspirone hydrochloride, chloral hydrate, disulfuram; tranquilizers: chloropromazine, promazine, fluphenzaine, other CNS stimulants: methylphenidate, cholinergics: rivastigmine.

In some aspects, the drug may be oxybutynin, buspirone, fentanyl, testosterone, progestin, estradiol, propentofylline, or a mixture thereof. It should be appreciated that one or more of these and other drugs described herein exist in many pharmaceutically acceptable salts. Examples of such salts include those generated by using inorganic agents (i.e., inorganic cations such as sodium, potassium, calcium, etc., and inorganic anions such as chloride, bromide, etc.,) and organic agents (i.e., organic cations such as piperazinyl, triazinyl, etc., and organic anions such as citrates, tartarates, tosylates, etc). In addition, these drugs are also present as polymorphs and/or isomers. Examples of polymorphs include monohydrates, dihydrates, hemi-hydrates, etc., as well those high-melting and low-melting polymorphs. These polymorphs can be characterized using X-ray crystallographic techniques or other well-known techniques in the art. Examples of isomers include geometric and optical isomers. Further, the pharmaceutical art has recognized that such salts, isomers, and polymorphs, as well as prodrugs, analogs, and metabolites for these drugs can be therapeutically effective as well and can be substituted with ease.

Examples of useful testosterone and related compounds include without limitation: testosterone, methyltestosterone, androstenedione, adrenosterone, dehydroepiandrosterone, oxymetholone, fluoxymesterone, methandrostenolone, testosterone, methyltestosterone, androstenedione, adrenosterone, dehydroepiandrosterone, oxymetholone, fluoxymesterone, methandrostenolone, testolactone, pregnenolone, 17α-methylnortestosterone, norethandrolone, dihydrotestosterone, danazol, oxymetholone, androsterone, nandrolone, stanozolol, ethylestrenol, oxandrolone, bolasterone and mesterolone, testosterone propionate, testosterone cypionate, testosterone phenylacetate, testosterone enanthate, testosterone acetate, testosterone buciclate, testosterone heptanoate, testosterone decanoate, testosterone caprate, testosterone isocaproate, and combinations thereof.

These testosterone compounds can be present in subsaturated concentrations, or low concentrations. Examples of compositions comprising subsaturated testosterone are known in the art. See, for example, U.S. Pat. Nos. 5,164,190, and 5,152,997, which are incorporated by reference in their entirety. These testosterone compositions and/or other sex hormones, such as estrogen, progestin, etc. can also be provided using carriers that are stable over long-term storage. Such compositions may comprise ethylhexylacrylate polymers, as described in U.S. Pat. No. 5,780,050, which is incorporated by reference herein. Methods for providing such hormones to males and females are also well known. See, U.S. Pat. Nos. 5,460,820, 5,152,997, and 5,783,208, which are incorporated by reference in their entirety. It is appreciated that using the disclosure of the present invention, one skilled in the art can readily accomplish the objective of the above-referenced patents.

Examples of useful estradiol and related compounds include without limitation 17β-estradiol, 17α-estradiol, conjugated equine estrogen, esterified estrogen, micronized estradiol, sodium estrogen sulfate, ethinyl estradiol, estrone, tibolone, selective estrogen receptor modulator (SERM), phytoestrogen, and mixtures thereof. Examples of useful progestin and related compounds include without limitation: progesterone, medroxy-progesterone acetate, norethindrone, and norethindrone acetate.

Examples of useful oxybutynin compounds include without limitation: N-desethyloxybutynin, (R)-oxybutynin, (S)-oxybutynin, (R)—N-desethyloxybutynin, and (S)—N-desethyloxybutynin. Particularly, it has been noted that the oxybutynin metabolite, N-desethyloxybutynin, as well as it (R)- and (S)-optical isomers exert an anticholinergic action that is equal to or greater than oxybutynin, and can be readily delivered for such a purpose. See, U.S. Pat. Nos. 5,411,740, 5,500,222, 5,532,278, 5,677,346, 5,686,097, 5,736,577, 5,747,065, 5,750,137, and 5,900,250, which are incorporated by reference in their entirety.

Transdermal delivery of oxybutynin using triacetin as a penetration enhancer has been described by U.S. Pat. Nos. 5,834,010, and 5,601,839, which are incorporated by reference in their entirety. Oxybutynin can be administered in low concentrations, such that the serum concentrations of one or more of its metabolites can be significantly lowered with the beneficial effect of reduced adverse drug reactions, such as anticholinergic effects (including dry mouth, constipation, blurred vision, etc.).

Examples of propentofylline compositions, which can be used in connection with the present invention, are described in U.S. Pat. No. 5,762,953, which is incorporated by reference in its entirety. It is appreciated that the transdermal penetration of such compositions may be further enhanced using the quaternary ammonium salt compounds of the present invention.

It is appreciated that any combination of any of the above drugs (that is one or more of any of the above drugs) may be used in this invention. The present invention also contemplates the use of such salts, isomers, polymorphs, prodrugs, analogs, and metabolites, including substances not specifically recited above.

It should also be recognized that the term "drug" as used herein refers to practically any chemical substance that has pharmacological activity or biological activity, as well as those substances that can be used for diagnostic or cosmetic purposes. Thus, vitamins, such as vitamin A, C, E, K, and various B complexes, veterinary drugs, and cosmetic agents such as wrinkle-reducing agents (including anti-oxidants, for example, ascorbic acid, ascorbyl palmitate, catechins, an polyphenol compounds), depilating agents (including calcium salt, thioglycolic acid, and calcium hydroxide), hair-growing agents (including relaxin, cyproterone acetate, spironolactor, flutamide, and minoxidil), depigmenting agents (including sulfites, bisulfites, and metabisulfites, and alkaline earth, and alkaline earth metal compounds thereof), are also included. Further, the term "drug" includes peptides, proteins, carbohydrates, fats, etc that are known to exert biological and or pharmacological effects.

It is appreciated that the above categories of drugs are not rigidly described and that one drug may be described accurately in more than one category or sub-category. For example, insulin may be described as a hormone, as an antidiabetic agent and also as a macromolecule.

Figure 7:
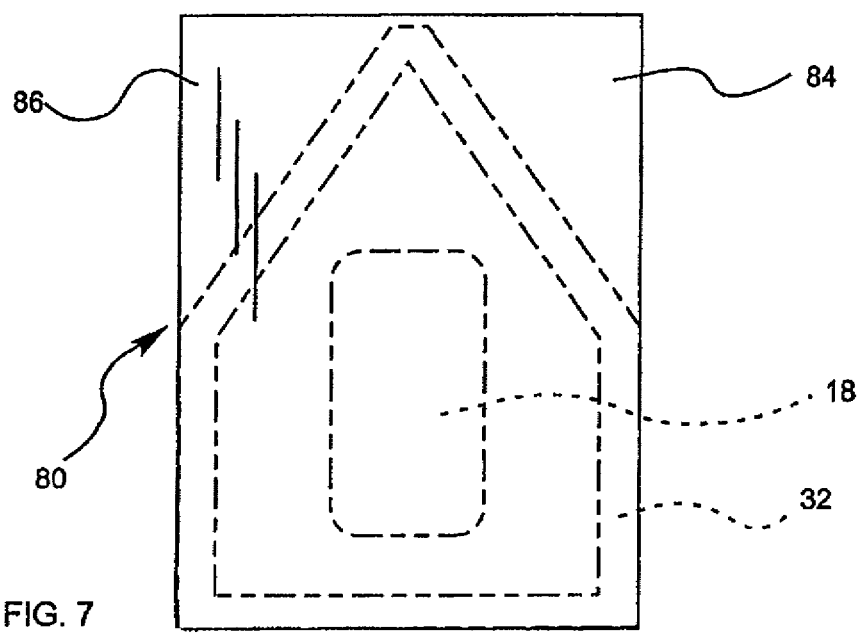
FIG. 7 is a front view of another embodiment of a peelable pouch in accordance with the present invention.
Figure 8:
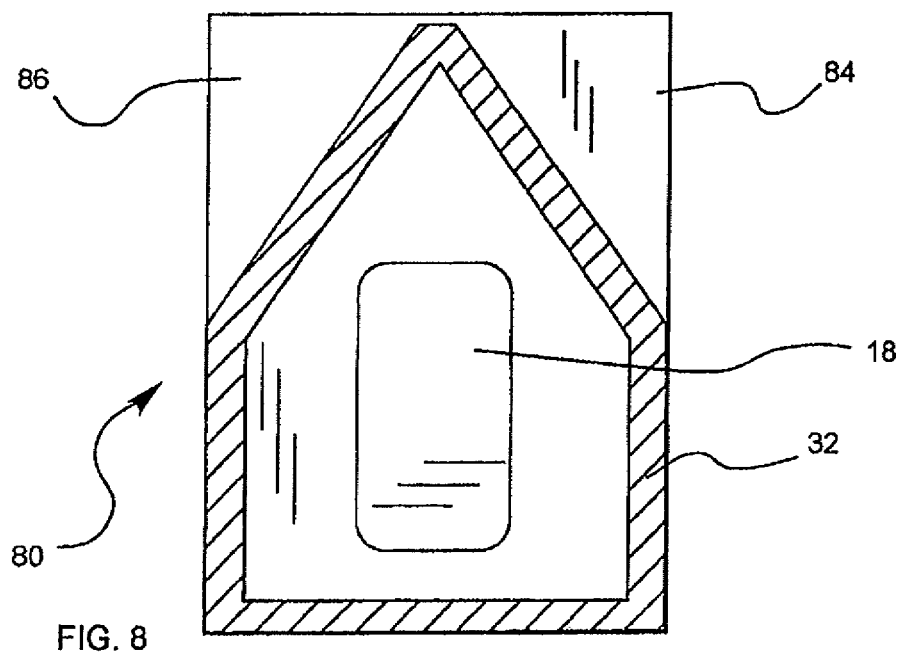
FIG. 8 is a front view of the peelable pouch of FIG. 7 with one ply of the pouch removed to reveal a transdermal patch therein.

Referring to FIGS. 7 and 8, another peelable pouch 80 in accordance with the present invention is shown which is similar in many respects as that described above. The pouch 80 includes more than one set of tabs, such as opposite first and second sets of tabs 84 and 86 formed on opposite sides of the pouch 80, so that the pouch can be opened from either side.

The pouches described above have rectangular or square shapes with four sides, while the seals form a pentagon shape or polygon with five sides within the perimeter of the rectangular shape of the pouch. Forming the five sided polygon seal within the perimeter of the rectangular pouch creates the tabs.

Referring to FIGS. 9a-9h, the pouch, seal, tabs, plies, and/or objects contained in the pouch can have other shapes. For example, the pouch can be shaped to conform to the shape of the object or patch contained therein. The pouch can be round or oval to eliminate sharp corners, as shown in FIGS. 9a-9d. It will be appreciated that the thinness of the plies combined with corners can form sharp edges that can be reduced by using round, oval, or curved pouches.

Figure 9A:
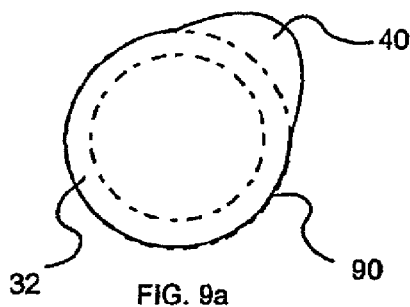
FIGS. 9a-9h are front views of other embodiments of a peelable pouch in accordance with the present invention.
Figure 9B:
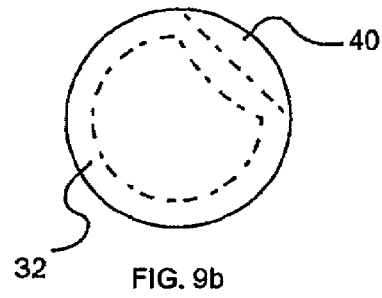

Referring to FIG. 9a, the pouch 90 can be substantially or mostly round, and have can have a substantially or mostly round seal 32. A portion of the pouch 90 can extend beyond the round or circular shape to form the tabs 40 that extend outside the circular shape. Referring to FIG. 9b, the pouch 91 and seal 32 similarly can be mostly round or circular. A portion of the seal 32 can be indented into the circular shape to form tabs 40 that are within the circular shape.

Figure 9C:
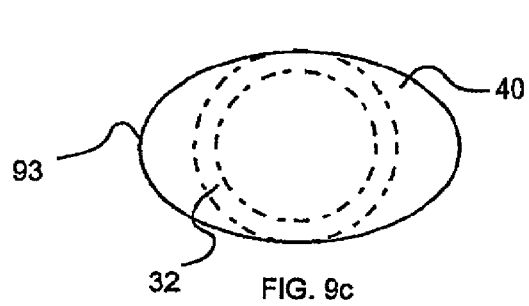
Figure 9D:
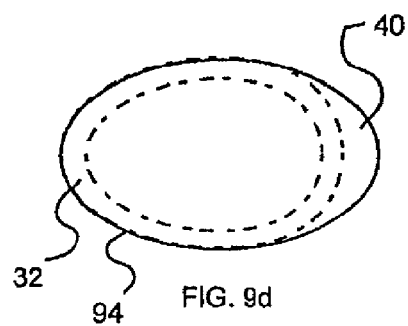

Referring to FIG. 9c, the pouch 93 can be substantially elliptical. The seal 32 can be substantially circular, thus forming tabs 40 at the distal ends of the elliptical pouch 93. Referring to FIG. 9d, the pouch 94 and seal 32 can be substantially elliptical. A portion of the seal 32 can indented into the elliptical shape to form tabs 40 that are within the elliptical shape.

Figure 9E:
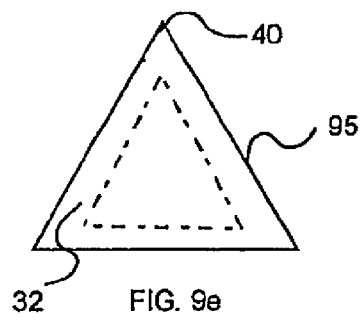
Figure 9F:
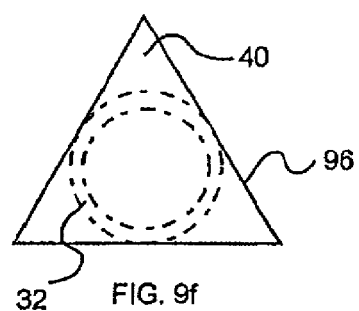

Referring to FIGS. 9e and 9f, the pouches can be triangular. Referring to FIG. 9e, the pouch 95 and seal 32 can be substantially triangular. A portion of the seal 32 can be indented into the elliptical shape to form tabs 40 that are within the triangular shape. Referring to FIG. 9f, the pouch 96 can be triangular while the seal 32 can be circular to create a plurality of tabs 40 around the pouch. Such a configuration can be easier to open because it can be opened from any corner of the triangular pouch 96.

Figure 9G:
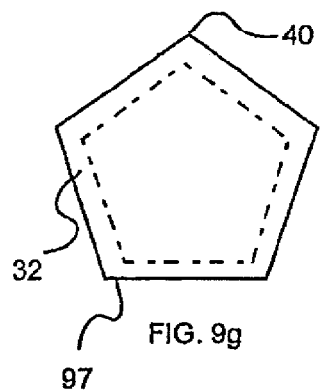
Figure 9H:
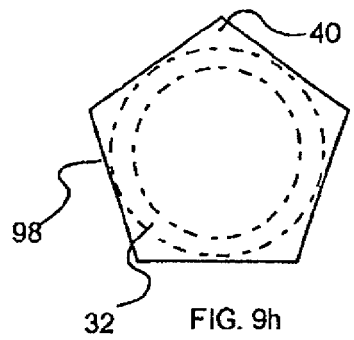

Referring to FIGS. 9g and 9h, the pouches can be a polygon, such as a pentagon. Referring to FIG. 9g, the pouch 97 and seal 32 can have a pentagonal shape. A portion of the seal can be indented to form tabs 40 within the pentagon. Referring to FIG. 9h, the pouch 98 can be pentagonal, while the seal 32 is circular, to form a plurality of tabs 40 about the pouch.

Figure 10:
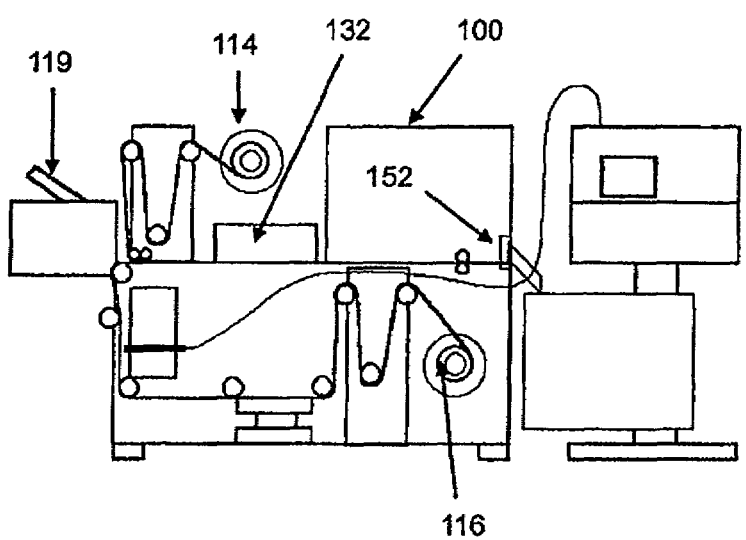
FIG. 10 is a schematic view of a machine and method for packaging transdermal patches in accordance with the present invention.
Figure 11:
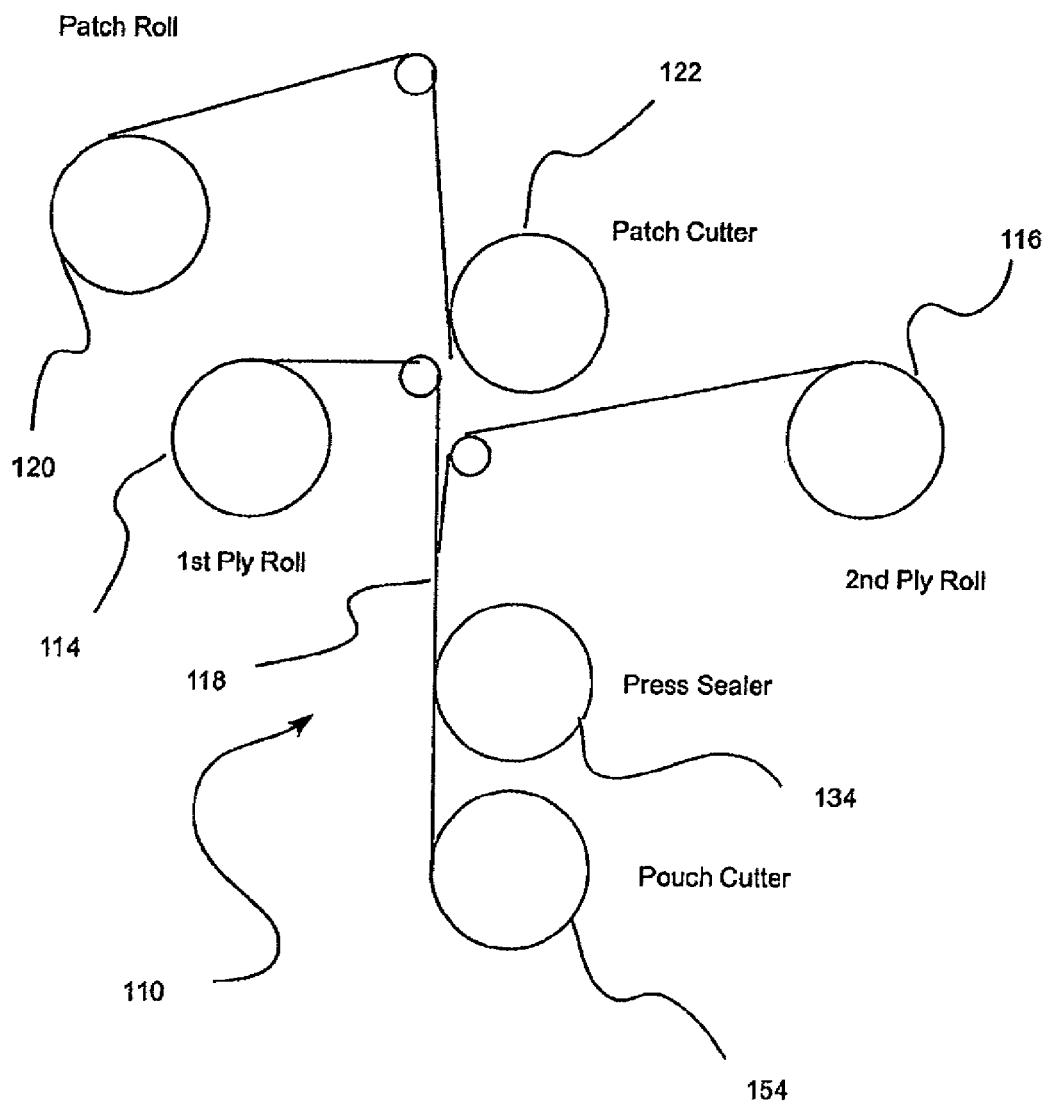
FIG. 11 is a schematic view of another machine and method for packaging transdermal patches in accordance with the present invention.

As illustrated in FIGS. 10 and 11, mechanisms are shown for packaging transdermal patches into the peelable pouches as described above. The mechanisms can operate intermittently or continuously, and can be oriented horizontally or vertically. For example, the mechanism 100 shown in FIG. 10 operates intermittently and is oriented horizontally, while the mechanism 110 shown in FIG. 11 operates continuously, and is oriented vertically. A method for packaging a transdermal patch 18 as described above can utilize such mechanisms. Such a method includes placing the transdermal patchs 18 between the first and second plies 22 and 24. The plies can be provided in continuous rolls of stock materials, such as first and second rolls 114 and 116, disposed on payouts of the mechanism. The rolls of material provide webs 118 between which, or upon which, the patches 18 can be disposed so that the patches are placed between the first and second plies. The rolls of material can be sized larger or wider than the actual pouches so that more than one pouch can be produced simultaneously by placing numerous patches between the plies in a spaced apart relationship.

Referring to FIG. 10, the packaging can be oriented horizontally with the webbing oriented horizontally so that the patches can be disposed onto one of the webs or plies. Thus, one of the rolls or payouts can be a lower roll or payout, while the other is an upper roll or payout. Alternatively, referring to FIG. 11, the packaging can be oriented vertically with the webbing oriented vertically so that the patches can be disposed between the webs or plies.

Referring to FIG. 10, the patches can be provided stacked in a cartridge 119 adjacent the webbing. One or more patches can be picked from the cartridge and placed on the web. Alternatively, referring to FIG. 11, the patches can be provided in a continuous roll 120 disposed on a payout of the mechanism. Individual patches can be separated or cut from the roll prior to the webbing, and placed thereon or therebetween. The mechanism can include a cutter with blades shaped to form the patches. The cutter can be a rolling cutter 122 with a cylindrical shape that makes rolling contact with the web to continuously cut or separate the patches from the web.

With the patches disposed between the webs or plies, at least a portion of the webs or plies are sealed together to form the enclosures about the patches. In one aspect, a seal is formed entirely around each patch. The plies are sealed by applying heat and pressure against the plies for a predetermined time period. The mechanisms can include a heat seal station 132 in which a press is movably disposed to selectively contact the plies. The press can be shaped and sized similar to a mold or blank of the seal. Thus, when the press contacts the plies, the seal is formed in the desired shape and size. The press can be configured to form numerous seals at the same time.

As shown in FIG. 10, the press 132 can be applied against the plies in a linear motion. Thus, the heat and pressure can be applied intermittently by the press. Alternatively, as shown in FIG. 11, the press 134 can be cylindrical and rotatably coupled to the mechanism to make rotating contact with the plies. Thus, the heat and pressure can be applied continuously, and the webbing can be run continuously. The press can have circular or arcuate molds or blanks of the seal formed therein.

Portions of the plies that extend beyond the seal or enclosure are left unsealed in order to form the tabs. The numerous pouches can be separated from one another and the webbing to form individual pouches with individual patches therein. The mechanisms can include a shearing station 150 for separating or cutting individual pouches from the webbing. As shown in FIG. 10, the mechanism can include blades 152 shaped and sized to cut the pouches from the webbing. The blades can include numerous blades to cut numerous pouches simultaneously. The blades can contact the webbing or plies linearly, like a press. Thus, the blades can operate intermittently. Alternatively, as shown in FIG. 11, the mechanism can include a cylindrical blade 154 rotatably coupled to the mechanism to make rolling contact with the webbing. Thus, the cylindrical blade can continuously cut the pouches from the webbing.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A medicine system, comprising:
   1) first and second opposing flexible plies forming an enclosure;
   2) a seal, extending along at least a portion of a perimeter of the opposing plies with an enclosed cavity between the plies;
   3) first and second opposing tabs, formed by a portion of the respective first and second opposing plies which extend beyond the seal;
   4) a transdermal matrix or liquid reservoir system patch, disposed in the enclosed cavity between the first and second opposing plies, comprising:
      a) a backing layer;
      b) a compound selected from the group consisting of:
         i) a salt of testosterone;
         ii) methyltestosterone, androstenedione, adrenosterone, dehydroepiandrosterone, oxymetholone, fluoxymesterone, methandrostenolone, testolactone, pregnenolone, 17a-methylnortestosterone, norethandrolone, dihydrotestosterone, danazol, androsterone, nandrolone, stanozolol, ethylestrenol, oxandrolone, bolasterone, mesterolone, testosterone propionate, testosterone cypionate, testosterone phenylacetate, testosterone enanthate, testosterone acetate, testosterone buciclate, testosterone heptanoate, testosterone decanoate, testosterone caprate, testosterone isocaprate and combinations thereof; and
         iii) combinations thereof;
      c) an adhesive layer with an exposed perimeter, wherein the adhesive layer comprises an adhesive; and
      d) a resilient release liner, removably attached over the adhesive layer so as to generate a spring force when displaced out of the flat configuration sufficient to overcome an adhesive force between the patch and one of the plies created by the adhesive layer leaking an adhesive from the exposed perimeter onto one of the plies;
   the seal including a resin; and
   the first and second opposing flexible plies having:
      i) a closed configuration in which a majority of the two plies are disposed in a planar layer; and
      ii) an open configuration in which at least a portion of the two plies are separated along the seal and pulled out of the planar layer and back across the planar layer to present the transdermal patch between the two plies.

2. The medicine system of claim 1, wherein the first and second opposing flexible plies form a pouch, and wherein the pouch comprises the enclosure.

3. The medicine system of claim 1, wherein the seal is formed by a process selected from the group consisting of chemical processes, mechanical processes, ultra-sonic welding processes and combinations thereof.

4. The medicine system of claim 3, wherein the seal is formed by the application of one selected from the group consisting of heat, pressure and combinations thereof.

5. The medicine system of claim 1, wherein the seal is corrugated, embossed or both.

6. The medicine system of claim 1, wherein the seal extends along substantially the entire perimeter of the plies.

7. The medicine system of claim 1, wherein a portion of the seal is indented from the perimeter of the plies.

8. The medicine system of claim 1, wherein the first and second plies are formed from the same or a different sheet of material.

9. The medicine system of claim 1, wherein at least one of the plies comprises an outer layer, a core layer and a laminate.

10. The medicine system of claim 9, wherein at least one of: (i) the outer layer comprises coated paper, (ii) the core layer comprises foil, and (iii) the laminate comprises low density polyethylene (LDPE).

11. The medicine system of claim 1, wherein at least one of the tabs is approximately the size of a fingertip.

12. The medicine system of claim 1, wherein the patch has a shape selected from the group consisting of rectangular, square, circular and oval.

13. The medicine system of claim 2, wherein the pouch has a shape selected from the group consisting of triangular, pentagonal, rectangular, square, round and oval.

14. The medicine system of claim 1, wherein the backing layer is at least one of opaque and occlusive.

15. The medicine system of claim 1, wherein the backing layer is selected from the group consisting of metal foils, metalized polyfoils, composite foils, films containing polyester, polyester, aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene copolymers, styrene-isoprene copolymers, polyethylene, polypropylene and combinations thereof.

16. The medicine system of claim 1, wherein the release liner is selected from the group consisting of metal foils, metalized polyfoils, composite foils, films containing polyester, polyester, aluminized polyester, polytetrafluoroethylene, polyether block amide copolymers, polyethylene methyl methacrylate block copolymers, polyurethanes, polyvinylidene chloride, nylon, silicone elastomers, rubber-based polyisobutylene, styrene, styrene-butadiene copolymers, styrene-isoprene copolymers, polyethylene, polypropylene and combinations thereof.

17. The medicine system of claim 1, wherein the adhesive layer includes at least one of a pressure sensitive adhesive and a biocompatible polymer.

18. The medicine system of claim 17, wherein the pressure sensitive adhesive is suitable for contact with skin for a time period selected from the group consisting of a few minutes to a few hours, less than one day, one day, more than one day, about 3-4 days and about 1-4 weeks.

19. The medicine system of claim 17, wherein the biocompatible polymer is a biocompatible adhesive polymer.

20. The medicine system of claim 1, wherein the adhesive is selected from the group consisting of acrylic adhesives, vinyl acetate adhesives, natural rubbers, synthetic rubbers, ethylenevinylacetate copolymers, polysiloxanes, polyacrylates, polyurethanes, plasticized weight polyether block amide copolymers, plasticized styrene-rubber block copolymers and combinations thereof.

21. The medicine system of claim 20, wherein the adhesive is selected from the group consisting of cross-linked acrylic copolymers, uncross-linked acrylic polymers, polyisobutylenes, neoprenes, polybutadienes, polyisoprenes and combinations thereof.

22. The medicine system of claim 1, wherein the adhesive comprises hexamethyleneglycol dimethacrylate, 2-ethyl hexylacrylate and N-vinyl pyrrolidone.

23. The medicine system of claim 1, wherein the transdermal patch is a matrix patch comprising a matrix, wherein the matrix comprises the compound.

24. The medicine system of claim 1, wherein the transdermal patch is a liquid reservoir system patch comprising a reservoir, wherein the reservoir comprises the compound.

25. The medicine system of claim 1, wherein the transdermal patch further comprises a permeation enhancer.

26. The medicine system of claim 25, wherein the permeation enhancer is selected from the group consisting of fatty acids, fatty acid esters, fatty alcohols, fatty acid esters of lactic acid or glycolic acids and their salts, amides, amines, pyrrolidones, glycerol trimesters, terpenes, classical surfactants, azocyclic compounds, organic acids, complexing agents, biologics and mixtures thereof.

\* \* \* \* \*